US00PP32942P2

(12) United States Plant Patent
Verduin

(10) Patent No.: US PP32,942 P2
(45) Date of Patent: Mar. 30, 2021

(54) ***ASTILBE* PLANT NAMED 'YOUANDME ALWAYS'**

(50) Latin Name: *Astilbe chinensis*
Varietal Denomination: Youandme Always

(71) Applicant: Harrie Verduin, Heemskerk (NL)

(72) Inventor: Harrie Verduin, Heemskerk (NL)

(73) Assignee: COMPASS PLANTS B.V., Hillegom (NL)

( * ) Notice: Subject to any disclaimer, the term of this patent is extended or adjusted under 35 U.S.C. 154(b) by 0 days.

(21) Appl. No.: 16/873,621

(22) Filed: May 21, 2020

(30) Foreign Application Priority Data

Feb. 1, 2020 (QZ) ..... PBR 20200350

(51) Int. Cl.
*A01H 5/02* (2018.01)
*A01H 6/80* (2018.01)

(52) U.S. Cl.
USPC ..... Plt./407

(58) Field of Classification Search
USPC ..... Plt./407
See application file for complete search history.

*Primary Examiner* — Susan McCormick Ewoldt
(74) *Attorney, Agent, or Firm* — C. Anne Whealy

(57) ABSTRACT

A new and distinct cultivar of *Astilbe* plant named 'Youandme Always', characterized by its broadly upright and mounding plant habit; vigorous growth habit; dense and bushy appearance; dark green-colored leaves; freely and uniformly flowering habit; red purple-colored flowers on strong, tall and upright peduncles; and good container and garden performance.

2 Drawing Sheets

Figure 1:
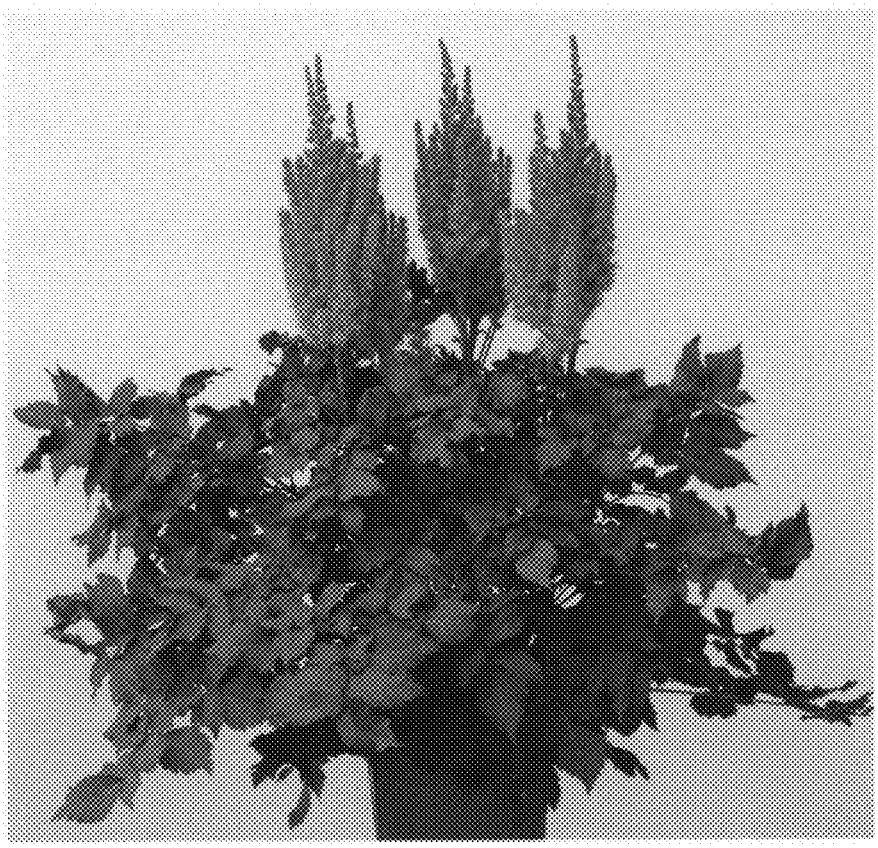

Botanical designation: *Astilbe chinensis.*
Cultivar denomination: 'YOUANDME ALWAYS'.

CROSS-REFERENCE TO A RELATED APPLICATION AND STATEMENT REGARDING PRIOR DISCLOSURES BY INVENTOR/APPLICANT

This application claims priority to a European Community Plant Breeders' Rights application filed on Feb. 1, 2020, application number 20200350. There have been no offers for sale anywhere in the world prior to the effective filing date of this Application and no accessibility to one of ordinary skill in the art could have been derived from the printed Plant Breeder's Rights documents.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Astilbe*, botanically known as *Astilbe chinensis* and hereinafter referred to by the name 'Youandme Always'.

The new *Astilbe* plant is a product of a planned breeding program conducted by the Inventor in Heemskerk, The Netherlands. The objective of the breeding program was to create new uniform and freely flowering *Astilbe* plants with attractive leaf and flower coloration.

The new *Astilbe* plant originated from a cross-pollination in 2013 in Heemskerk, The Netherlands, of two unidentified *Astilbe chinensis* seedling selections. The new *Astilbe* plant was discovered and selected by the Inventor as a single flowering plant from within the progeny of the stated cross-pollination in a controlled greenhouse environment in Heemskerk, The Netherlands during the summer of 2015.

Asexual reproduction of the new *Astilbe* plant by vegetative divisions in a controlled nursery environment in Heemskerk, The Netherlands since December, 2015, has shown that the unique features of this new *Astilbe* plant are stable and reproduced true to type in successive generations.

SUMMARY OF THE INVENTION

Plants of the new *Astilbe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Youandme Always'. These characteristics in combination distinguish 'Youandme Always' as a new and distinct *Astilbe* plant:

1. Broadly upright and mounding plant habit.
2. Vigorous growth habit.
3. Dense and bushy appearance.
4. Dark green-colored leaves.
5. Freely and uniformly flowering habit.
6. Red purple-colored flowers on strong, tall and upright peduncles.
7. Good container and garden performance.

Plants of the new *Astilbe* differ primarily from plants of the parent selections in plant habit as plants of the new

*Astilbe* are more compact than plants of the parent selections. In addition, inflorescences of plants of the new *Astilbe* are longer and broader than inflorescences of plants of the parent selections.

Plants of the new *Astilbe* can be compared to plants of *Astilbe chinensis* 'Vision in Pink', disclosed in U.S. Plant Pat. No. 11,860. In side-by-side comparisons, plants of the new *Astilbe* and 'Vision in Pink' differ primarily in the following characteristics:

1. Plants of the new *Astilbe* are shorter than plants of 'Vision in Pink'.
2. Inflorescences of plants of the new *Astilbe* are smaller than inflorescences of plants of 'Vision in Pink'.
3. Flowers of plants of the new *Astilbe* are red purple in color whereas flowers of plants of 'Vision in Pink' are bright pink in color.

Plants of the new *Astilbe* can also be compared to plants of *Astilbe chinensis* 'Loud and Proud', not patented. In side-by-side comparisons, plants of the new *Astilbe* and 'Loud and Proud' differ primarily in the following characteristics:

1. Plants of the new *Astilbe* are shorter than plants of 'Loud and Proud'.
2. Inflorescences of plants of the new *Astilbe* are smaller than inflorescences of plants of 'Loud and Proud'.
3. Flowers of plants of the new *Astilbe* are red purple in color than flowers of plants of 'Loud and Proud' which are purple in color.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet (FIG. 1 of 2) is a side perspective view of a typical flowering plant of 'Youandme Always' grown in a container.

Figure 2:
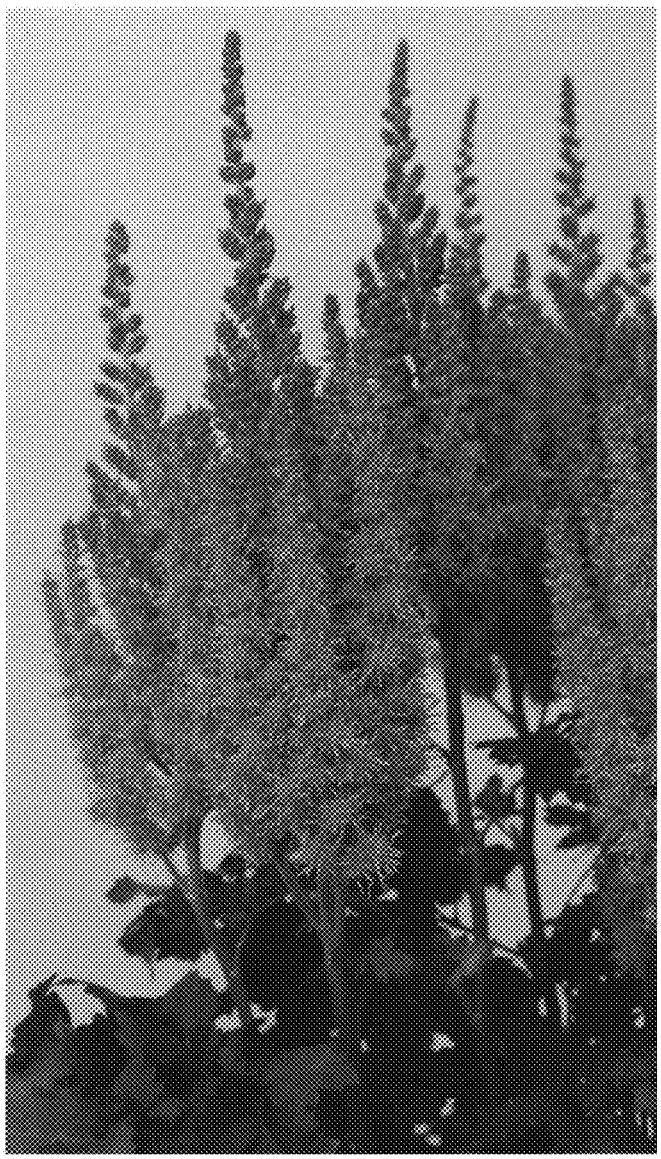

The photograph on the second sheet (FIG. 2 of 2) is a close-up view of typical inflorescences of 'Youandme Always'.

DETAILED BOTANICAL DESCRIPTION

The aforementioned photographs and following observations, measurements and values describe plants grown during the late summer in 19-cm containers in an outdoor nursery in Heemskerk, The Netherlands and under cultural practices typical of commercial *Astilbe* production. During the production of the plants, day temperatures ranged from 20° C. to 40° C. and night temperatures ranged from 8° C. to 24° C. Plants were one year old when the photographs and description were taken. In the following description, color references are made to The Royal Horticultural Society Colour Chart, 2015 Edition, except where general terms of ordinary dictionary significance are used.

Botanical classification: *Astilbe chinensis* 'Youandme Always'.

Parentage:

*Female, or seed, parent*.—Unidentified *Astilbe chinensis* seedling selection, not patented.

*Male, or pollen, parent*.—Unidentified *Astilbe chinensis* seedling selection, not patented.

Propagation:

*Type*.—By vegetative divisions.

*Time to initiate roots*.—About three weeks at temperatures about 20° C.

*Root description*.—Thick, fleshy; typically brown in color, actual color of the roots is dependent on substrate composition, water quality, fertilizer type and formulation.

*Rooting habit*.—Freely branching; dense.

Plant description:

*Plant form and growth habit*.—Herbaceous perennial; broadly upright and mounding plant form with inflorescences held above the foliar plane; flowering stems and leaves basal; freely flowering with numerous basal branches developing per plant, dense and bushy; vigorous growth habit; and freely and uniformly flowering habit.

*Growth rate*.—Moderately rapid to rapid; from divisions, about three months are required to produce fully-grown flowering plants in containers.

*Plant height* (*soil level to top of foliar plane*).—About 36.4 cm.

*Plant height* (*soil level to top of inflorescences*).—About 61 cm.

*Plant width* (*spread*).—About 80 cm.

*Stem description*.—Length: About 32.3 cm. Diameter: About 7 mm. Internode length: About 5.8 cm. Strength: Strong. Aspect: Erect to about 10° from vertical. Texture and luster: Moderately pubescent; moderately glossy. Color, developing: Close to 152A. Color, developed: Close to 144A.

Leaf description:

*Arrangement*.—Alternate; biternately compound; on average, about 27 leaflets per leaf.

*Leaf length* (*excluding petiole*).—About 28.9 cm.

*Leaf width*.—About 32 cm.

*Terminal leaflet length*.—About 7 cm.

*Terminal leaflet width*.—About 5 cm.

*Lateral leaflet length*.—About 4.7 cm.

*Lateral leaflet width*.—About 2.9 cm.

*Leaf shape, in outline*.—Deltoid to broadly deltoid.

*Leaflet shape*.—Ovate to broadly ovate.

*Leaflet apex*.—Apiculate.

*Leaflet base*.—Attenuate to obtuse.

*Leaflet margin*.—Biserrate.

*Leaflet texture and luster, upper and lower surfaces*.—Sparsely pubescent; slightly glossy.

*Leaflet venation pattern*.—Pinnate.

*Leaflet color*.—Developing leaflets, upper surface: Close to 138A. Developing leaflets, lower surface: Close to 138B. Fully expanded leaflets, upper surface: Close to NN137A to NN137B; venation, close to 143B. Fully expanded leaflets, lower surface: Close to 147B; venation, close to 144B.

*Leaf petiole length*.—About 34.5 cm.

*Leaf petiole diameter*.—About 3 mm.

*Leaf and leaflet petiole strength*.—Strong.

*Leaf and leaflet petiole texture and luster, upper and lower surfaces*.—Moderately pubescent; moderately glossy.

*Leaf and leaflet petiole color, upper surface*.—Close to 144A; towards the base, close to 144B; at the nodes, tinged with close to 176A to 176B.

*Leaf and leaflet petiole color, lower surface*.—Close to 144B.

Flower description:

*Flower type and flowering habit*.—Single rotate flowers arranged on terminal compound panicles; flowers face upright, outward or downward depending on position on the inflorescence; panicles conical in shape; freely and uniformly flowering habit with about 4,500 flowers developing per inflorescence and about 35,000 flowers developing per plant during the flowering season.

*Fragrance*.—Faint; moldy.

*Natural flowering season*.—Plants begin flowering about 13 weeks after planting; continuously flowering from late spring until late summer in The Netherlands.

*Postproduction longevity*.—Flowers last about ten days on the plant; flowers not persistent.

*Flower buds*.—Height: About 1.5 mm. Diameter: About 1.5 mm. Shape: Roughly spherical. Texture and luster: Smooth, glabrous; matte. Color: Sepals, close to 148C and petals, close to 60C.

*Inflorescence height*.—About 26.6 cm.

*Inflorescence diameter*.—About 8.4 cm.

*Flower diameter*.—About 1.8 cm.

*Flower depth*.—About 8 mm.

*Petals*.—Quantity per flower: Typically five in a single whorl. Length: About 7 mm. Width: About 0.9 mm. Shape: Oblanceolate. Apex: Bluntly acute. Base: Narrowly cuneate. Margin: Entire; not undulate. Texture and luster, upper and lower surfaces: Smooth, glabrous; matte. Color: Developing petals, upper and lower surfaces: Close to 64B. Fully expanded petals, upper and lower surfaces: Close to 70B; with development, color becoming closer to 70C.

*Sepals*.—Quantity per flower: Typically five in a single whorl, lower 30% fused towards the base forming a campanulate-shaped calyx. Length: About 2 mm. Width: About 0.9 mm. Shape: Ovate. Apex: Acute. Base: Cuneate, fused. Margin: Entire. Texture and luster, upper and lower surfaces: Smooth, glabrous; matte. Color: Developing sepals, upper and lower surfaces: Close to 147D; towards the margins, close to 60D. Fully expanded sepals, upper and lower surfaces: Close to 69D; towards the apex, close to 70D; colors do not change with development.

*Peduncles*.—Length: About 34.2 cm. Diameter: About 4 mm. Angle: Mostly erect. Strength: Strong. Texture and luster: Densely pubescent; slightly glossy. Color: Close to 144B to 144C.

*Pedicels*.—Length: About 0.5 mm. Diameter: About 0.5 mm. Angle: About 45° from peduncle axis. Strength: Moderately strong. Texture and luster: Moderately pubescent; matte. Color: Close to 64C.

*Reproductive organs*.—Stamens: Quantity per flower: Typically ten; anthers basifixed. Filament length: About 2 mm. Filament color: Close to 75B. Anther shape: Broadly ovate. Anther length: About 0.4 mm. Anther diameter: About 0.25 mm. Anther color: Close to 68C. Pollen amount: Scarce. Pollen color: Close to 156D. Pistils: Quantity per flower: Two. Pistil length: About 1.75 mm. Stigma diameter: About 0.1 mm. Stigma shape: Club-shaped. Stigma color: Close to 60C to 60D. Style length: About 1.5 mm. Style color: Close to 73B to 73C. Ovary color: Close to 73C.

*Seeds and fruits*.—To date, seed and fruit development have not been observed on plants of the new *Astilbe*.

Pathogen & pest resistance: To date, plants of the new *Astilbe* have not been noted to be resistant to pathogens and pests common to *Astilbe* plants.

Garden performance: Plants of the new *Astilbe* have been observed to have good garden performance and tolerate rain, wind, temperatures ranging from about −25° to 35° C. and to be suitable for USDA Hardiness Zones 5 through 10.

It is claimed:

1. A new and distinct *Astilbe* plant named 'Youandme Always' as illustrated and described.

* * * * *